United States Patent [19]

McRae

[11] Patent Number: Plant 6,475

[45] Date of Patent: Dec. 20, 1988

[54] LILY NAMED 'SWAN SONG'

[75] Inventor: Edward A. McRae, Boring, Oreg.

[73] Assignee: Melridge, Inc., Gresham, Oreg.

[21] Appl. No.: 23,772

[22] Filed: Mar. 9, 1987

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Charles W. Rummler

[57] ABSTRACT

A new variety of hybrid lily plant bearing large, upright to semi-upright flowers of excellent form particularly characterized by their completely unspotted and pure white coloration. This combination of pure white coloration, large size and substance, and the upright to semi-upright orientation of the flowers is completely new in the Oriental hybrid divisions of lilies suited to forcing and to mass commercial cultivation. This plant is highly resistant to disease and shows tolerance of virus; it is an excellent garden plant; and the bulbs may be precooled and forced for cut flower production.

1 Drawing Sheet

BACKGROUND OF THE NEW PLANT

This new variety of lily plant originated as a seedling which first flowered at Sandy, Oreg., in 1970, the mother plant for this seedling having resulted from my crossing, at Sandy, Oreg., a clonal selection from the 'Pink Glory' strain with a plant selected from the species *Lilium nobilissum* as the pollen plant; this crossing having been done with the object of producing large flowered, upright and semi-upright Oriental hybrids in the shades of soft pink and white suited to forcing into flower out-of-season, an accomplishment heretofore unknown in the lily breeding art. The crossing of these distinctively related parent plants was successfully accomplished in greenhouse where the temperatures were maintained extremely high for at least one week after pollination. This distinctive pure white seedling was asexually reproduced by me and under my direction at Sandy, Oreg., with completely satisfactory results and successive generations produced by natural propagation from bulblets, by bulb scale propagation and by tissue culturing from bulb scale explants, have demonstrated that the novel and distinctive characteristics of this new lily variety hold true under asexual propagation from generation to generation and appear to be firmly fixed. This new Oriental lily hybrid with the upright to semi-upright orientation of its extremely large sized and broad tepalled "bowl-shaped" flowers and its completely unspotted pure white coloration is a combination unique among Oriental hybrid lilies. The plant possesses unusually strong, stout stems, and exceptionally broad leaves; and additionally, the clone possesses to a high degree the desirable characteristics of hybrid vigor, great hardiness, and disease resistance, as well as excellence of form, color, and habit as observed at Sandy, Oregon.

We have found this new variety to be well suited to forcing out-of-season when the bulbs are dug at the appropriate time and properly precooled. Bulbs dug in late October and properly precooled and potted in January will flower under glass in western Oregon in an average of one hundred to one hundred fifteen days with no supplementary lighting and at moderate greenhouse temperatures.

DESCRIPTION OF THE DRAWING

This new variety of lily plant is illustrated by the accompanying photographic drawing which shows the open bloom in full color and illustrates the flower form, the tepal arrangements, its upright to semi-upright orientation, and its completely unspotted pure white coloration, the colors shown being as nearly true to those herein specified as is reasonably possible to obtain by conventional professional photographic procedures.

DESCRIPTION OF THE NEW VARIETY

The following is a detailed description of my new variety of Asiatic hybrid lily with nomenclature according to The International Lily Register, 2nd edition, 1969 (The Royal Horticultural Society of London, England), and with color designations according to The R.H.S. Colour Chart published by the society in 1966.

THE PLANT

Origin: Seedling.

Parentage:

- *Seed parent.*—A selected clone from the 'Pink Glory' strain (unpatented).
- *Pollen parent.*—A selected clone of *Lilium nobilissum* (unpatented).

Classification:

- *Botanic.*—Division VII-B, bowl-shaped Oriental hybrid lily, according to The Horticultural Classification of Lilies (The Royal Horticultural Society of London, England).
- *Commercial.*—Hybrid Oriental Lily.

Form: Single stem, erect and stately.

Height: About 70 to 125 cm. from bulbs of about 14 to 18 cm. in circumference; provided that their light levels are adequate. Low light levels may cause "stretching".

Growth: Vigorous and upright.

Foliage:

- *Quantity.*—Abundant.
- *Size of leaf.*—Unusually broad. About 12 to 15 cm. long and about 7 to 8 cm. wide.
- *Shape of leaf.*—Generally elliptical with acuminate tip.
- *Texture.*—Leathery.
- *Aspect.*—Glossy.
- *Color.*—Medium green, lighter on the lower side.

The bulb:

- *Size.*—Variable, ranging to about 25 cm. in circumference in commercial use.
- *Color.*—White, with flushes of soft pink or soft yellow after exposure to light.

THE BUD

Form: Long ovoid with rounded base and obtuse tip.
Size: About 9 to 12 cm. long and about 10 to 12 cm. in circumference just prior to opening.
Opening rate: The bud opens slowly, taking about one hour in response to morning light.
Color: White, with soft green midribs.
Peduncle:
*Length.*—Averages about 4 to 6 cm., but may elongate if light levels are too low or if the bulbs have been improperly stored prior to forcing.
Color: Medium green with very light plum overlay.

THE FLOWER

Blooming habit: Once, annually and profusely in mid-season.
Size: Large, averaging about 18 to 23 cm. in diameter, reflexing at the tepal tips on the second day to make the flower spread about 15 to 18 cm. in diameter.
Borne: In a single raceme inflorescence having from three to six flowers from a bulb of about 14 to 16 cm. in circumference.
Shape: Becomes a broad bowl shape by the second day with the "bowl" about 10 cm. deep.
Tepalage: Typical of genus Lilium with six imbricated tepals in hexagonal arrangement.
*Color.*—The tepals are distinguished by their pure white coloration, the nectary furrows being of apple green color.
*Spotting.*—The flowers are completely unspotted.
*Aspect.*—Shiny.
*Longevity.*—The tepals stay on the stems about three weeks.
Pedicel:
*Length.*—About 8 to 12 cm., in average.
*Character.*—Sturdy and ascending up to 45 degrees from the horizontal.
*Color.*—Medium green with very light plum overlay.
Color changes: None.
Disease resistance: The flower and plant are resistant to disease; in particular, they are resistant to Fusarium bulb rot and Botrytis blight.

Lasting quality: The flower is long lasting, both on the plant and as a cut flower.

REPRODUCTIVE ORGANS

Stamens:
*Number.*—Six, with arrangement typical of genus Lilium.
*Anthers (dehisced) and pollen.*—Color: Grayed red, 179A.
*Filaments.*—Length: About 5 cm. Color: Soft green to white.
Pistil:
*Number.*—One.
*Style.*—About 5 cm. long.
*Stigma.*—Size: Large. Color: Soft greenish-white to very light pink.
Character of ovary: The ovary characteristic is that of the genus Lilium.

THE FRUIT

Fertility: The fruit is fertile.
Shape: Ovoid.
Color at maturity: Soft brown, sometimes overlaid with soft plum.

My new variety of Asiatic hybrid lily most nearly resembles *Lilium nobilissum* but is taller, with stronger stems and its flowers are not as completely upfacing as those of *Lilium nobilissum.* Its flower form is larger, more conspicuously broader-tepalled, more bowl-shaped, and less trumpet-formed.

I claim:

1. A new and distinctive variety of Oriental hybrid lily plant and the parts thereof, substantially as herein shown and described, characterized by its unique upright to semi-upright flower orientation, the pure white unspotted flower coloration, and the excellence of its flower form; by its high resistance to disease, its tolerance of virus, and its versatility both as a garden plant and as a cut flower producer from precooled bulbs forced under glass out-of-season.

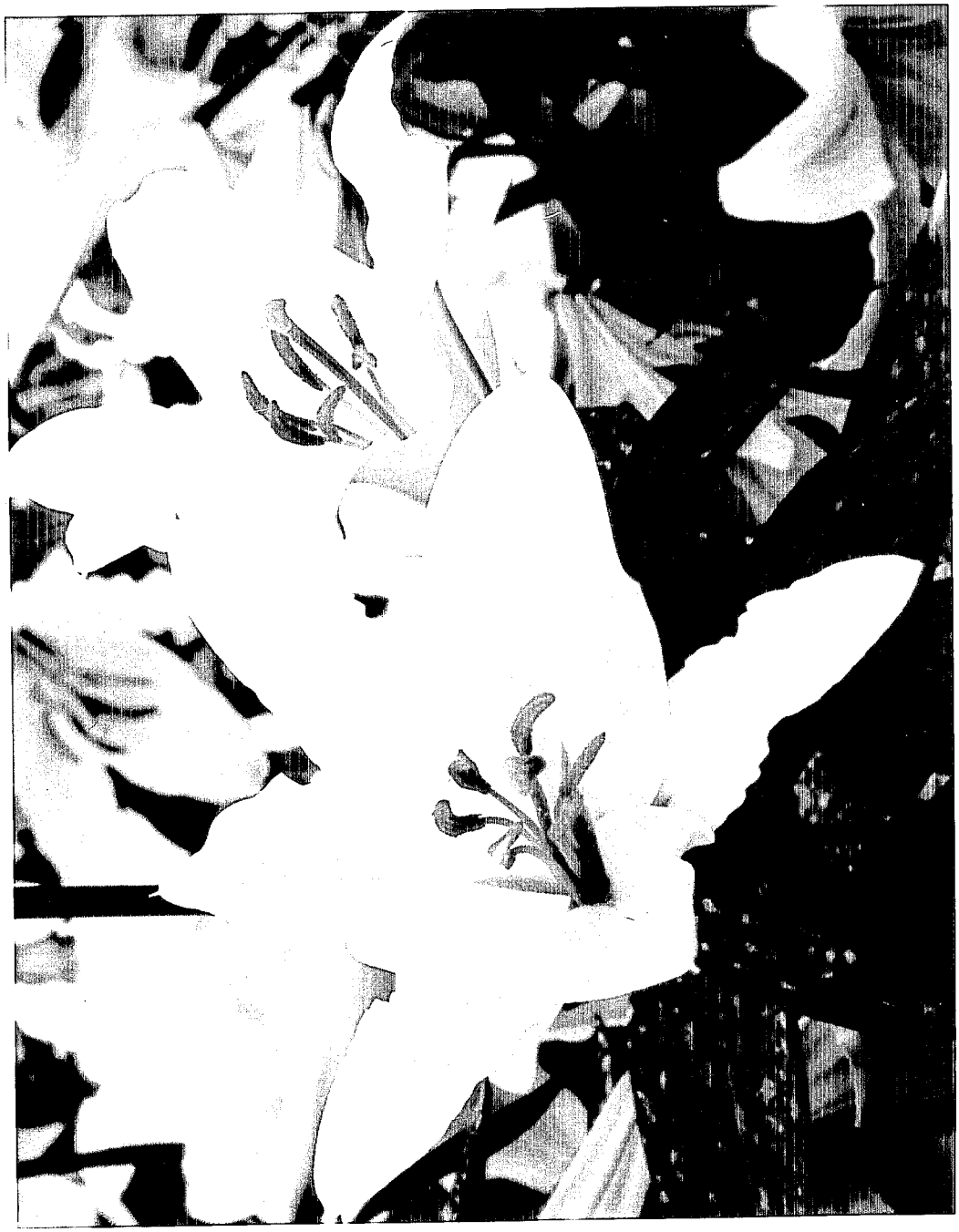

* * * * *